(12) United States Patent
Lotteau et al.

(10) Patent No.: US 9,168,236 B2
(45) Date of Patent: Oct. 27, 2015

(54) METHODS AND PHARMACEUTICAL COMPOSITIONS FOR INHIBITING INFLUENZA VIRUSES REPLICATION

(75) Inventors: Vincent Lotteau, Lyons (FR); Benoit De Chassey, Lyons (FR); Patrice Andre, Lyons (FR); Laurene Meyniel-Schicklin, Lyons (FR); Anne Aublin-Gex, Lyons (FR)

(73) Assignees: Institut National de la Santé et de la Recherche Médicale (INSERM), Paris (FR); Université Claude Bernard - Lyon 1, Villeurbanne Cedex (FR)

( * ) Notice: Subject to any disclaimer, the term of this patent is extended or adjusted under 35 U.S.C. 154(b) by 0 days.

(21) Appl. No.: 14/110,214

(22) PCT Filed: Apr. 10, 2012

(86) PCT No.: PCT/EP2012/056467
§ 371 (c)(1),
(2), (4) Date: Oct. 7, 2013

(87) PCT Pub. No.: WO2012/136851
PCT Pub. Date: Oct. 11, 2012

(65) Prior Publication Data
US 2014/0030224 A1    Jan. 30, 2014

(30) Foreign Application Priority Data

Apr. 8, 2011 (EP) .................................... 11305410

(51) Int. Cl.
*A61K 39/145* (2006.01)
*A61K 31/198* (2006.01)
(Continued)

(52) U.S. Cl.
CPC .............. *A61K 31/198* (2013.01); *A61K 31/122* (2013.01); *A61K 31/337* (2013.01);
(Continued)

(58) Field of Classification Search
None
See application file for complete search history.

(56) References Cited

U.S. PATENT DOCUMENTS

2004/0053858 A1* 3/2004 Berg ................................ 514/27
2007/0270362 A1* 11/2007 Harlan et al. .................... 514/44
(Continued)

FOREIGN PATENT DOCUMENTS

| WO | 98/30228 A1 | 7/1998 |
| WO | 2004/106328 A1 | 12/2004 |
| WO | WO 2006029081 | * 3/2006 |

OTHER PUBLICATIONS

Schwarz, "Oxidative Stress During Viral Infection," Free Radical Biology & Medicine, vol. 21, No. 5: 641-649 (1996).*

*Primary Examiner* — Zachariah Lucas
*Assistant Examiner* — M. Franco Salvoza
(74) *Attorney, Agent, or Firm* — Whitham, Curtis, Christofferson & Cook, P.C.

(57) ABSTRACT

The present invention relates to methods and pharmaceutical compositions for inhibiting influenza virus replication. More particularly, the present invention relates to a compound selected from the group consisting of Gemcitabine, Obatoclax Mesylate, Docetaxel, HA-14, Alsterpaullone, GSK3B inhibitor VIII, GSK3B inhibitor XV, Indirubin 3'-monoxime, L glutathione reduced, Fluocinolone acetonide, Tirofiban, Topotecan hydrochloride, Clofarabine, Vinblastine, Menadione Crystalline and derivatives or analogues thereof for use in the treatment of an influenza infection in a subject in need thereof.

10 Claims, 15 Drawing Sheets

Figure 1:
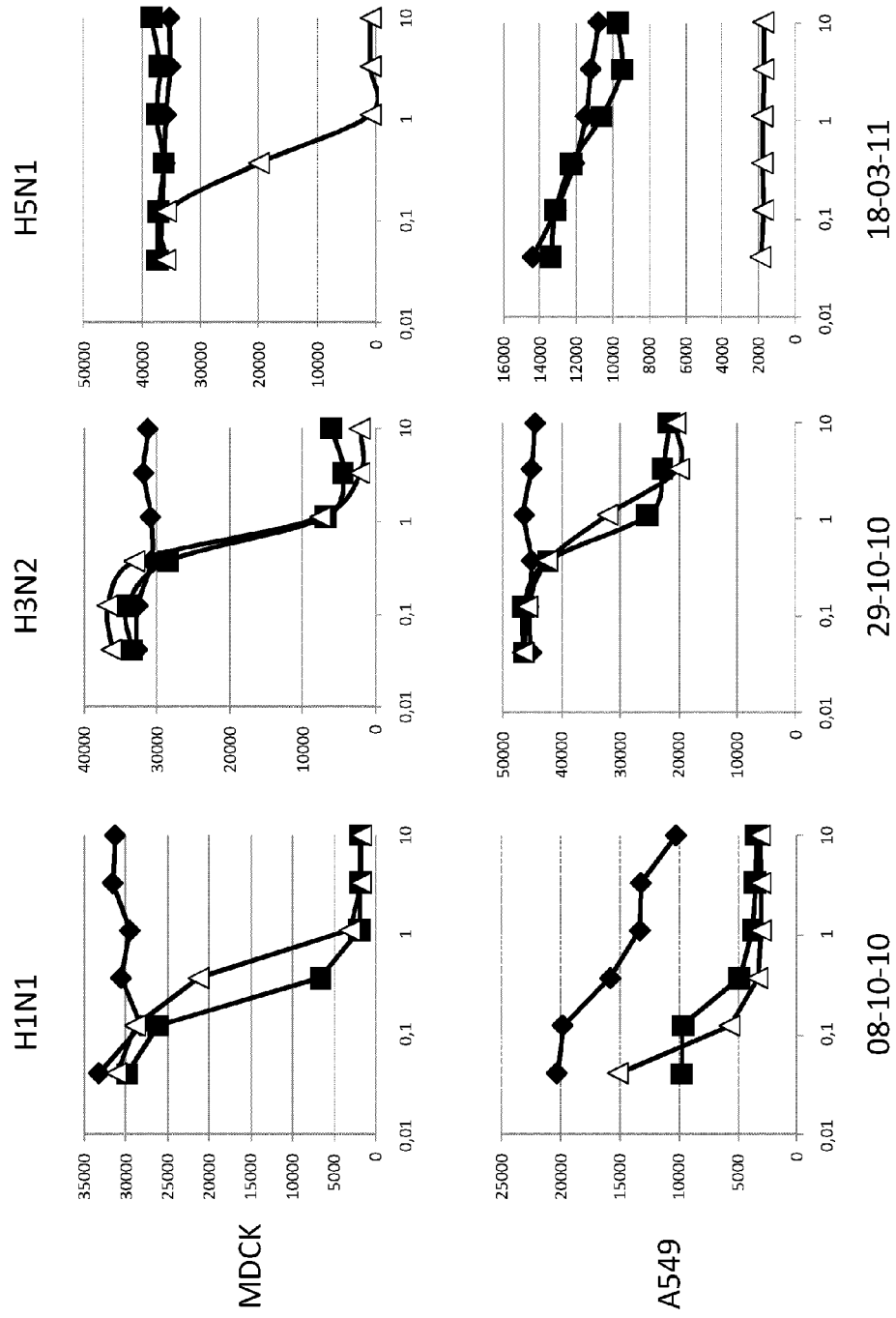

(51) Int. Cl.
- *A61K 31/122* (2006.01)
- *A61K 31/337* (2006.01)
- *A61K 31/352* (2006.01)
- *A61K 31/404* (2006.01)
- *A61K 31/426* (2006.01)
- *A61K 31/4465* (2006.01)
- *A61K 31/4745* (2006.01)
- *A61K 31/475* (2006.01)
- *A61K 31/55* (2006.01)
- *A61K 31/555* (2006.01)
- *A61K 31/58* (2006.01)
- *A61K 31/7068* (2006.01)
- *A61K 31/7076* (2006.01)
- *A61K 38/06* (2006.01)
- *A61K 45/06* (2006.01)
- *A61K 38/00* (2006.01)
- *A61K 38/21* (2006.01)

(52) U.S. Cl.
CPC ............. *A61K31/352* (2013.01); *A61K 31/404* (2013.01); *A61K 31/426* (2013.01); *A61K 31/4465* (2013.01); *A61K 31/475* (2013.01); *A61K 31/4745* (2013.01); *A61K 31/55* (2013.01); *A61K 31/555* (2013.01); *A61K 31/58* (2013.01); *A61K 31/7068* (2013.01); *A61K 31/7076* (2013.01); *A61K 38/005* (2013.01); *A61K 38/063* (2013.01); *A61K 38/21* (2013.01); *A61K 45/06* (2013.01)

(56) References Cited

U.S. PATENT DOCUMENTS

2010/0069309 A1* 3/2010 Gage ............................... 514/18
2012/0172285 A1* 7/2012 Walensky et al. .............. 514/1.4

* cited by examiner

METHODS AND PHARMACEUTICAL COMPOSITIONS FOR INHIBITING INFLUENZA VIRUSES REPLICATION

FIELD OF THE INVENTION

The present invention relates to methods and pharmaceutical composition for inhibiting influenza virus replication.

BACKGROUND OF THE INVENTION

Influenza viruses are one of the most ubiquitous viruses present in the world, affecting both humans and livestock. Influenza results in an economic burden, morbidity and even mortality, which are significant.

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of host-derived lipid material. Influenza virus comprises two surface antigens, glycoproteins neuraminidase (NA) and haemagglutinin (HA), which appear as spikes, 10 to 12 nm long, at the surface of the particles. It is these surface proteins, particularly the haemagglutinin that determine the antigenic specificity of the influenza subtypes. Virus strains are classified according to host species of origin, geographic site and year of isolation, serial number, and, for influenza A, by serological properties of subtypes of HA and NA. 16 HA subtypes (HI-HI6) and nine NA subtypes (N1-N9) have been identified for influenza A viruses. Viruses of all HA and NA subtypes have been recovered from aquatic birds, but only three HA subtypes (HI, H2, and H3) and two NA subtypes (N1 and N2) have established stable lineages in the human population since 1918. Only one subtype of HA and one of NA are recognised for influenza B viruses.

Influenza A viruses evolve and undergo antigenic variability continuously. A lack of effective proofreading by the viral RNA polymerase leads to a high rate of transcription errors that can result in amino-acid substitutions in surface glycoproteins. This is termed "antigenic drift". The segmented viral genome allows for a second type of antigenic variation. If two influenza viruses simultaneously infect a host cell, genetic reassortment, called "antigenic shift" may generate a novel virus with new surface or internal proteins. These antigenic changes, both 'drifts' and 'shifts' are unpredictable and may have a dramatic impact from an immunological point of view as they eventually lead to the emergence of new influenza strains and that enable the virus to escape the immune system causing the well known, almost annual, epidemics. Both of these genetic modifications have caused new viral variants responsible for pandemic in humans.

Influenza viruses cause epidemics almost every winter, with infection rates for type A or B virus as high as 40% over a six-week period. Influenza infection results in various disease states, from a sub-clinical infection through mild upper respiratory infection to a severe viral pneumonia. Typical influenza epidemics cause increases in incidence of pneumonia and lower respiratory disease as witnessed by increased rates of hospitalization or mortality. The severity of the disease is primarily determined by the age of the host, his immune status and the site of infection.

Elderly people, 65 years old and over, are especially vulnerable, accounting for 80-90% of all influenzarelated deaths in developed countries. Individuals with underlying chronic diseases are also most likely to experience such complications. Young infants also may suffer severe disease. These groups in particular therefore need to be protected. Besides these 'at risk'-groups, the health authorities are also recommending to vaccinate healthy adults who are in contact with elderly persons.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective. Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Antiviral drugs (e.g. neuraminidase inhibitors or M2 inhibitors) can also be used to treat influenza, but viruses can develop resistance to the standard antiviral drugs. Thus, there is still a need for drugs for treating influenza infections, such as for drugs with reduced sensitivity to viral titer.

SUMMARY OF THE INVENTION

The present invention relates to methods and pharmaceutical composition for inhibiting influenza virus replication.

More particularly, the present invention relates to a method for inhibiting the replication capacity of an influenza virus in an infected cell comprising the steps consisting contacting said infected cell with a least one compound selected from the group consisting of Gemcitabine, Obatoclax Mesylate, Docetaxel, HA-14, Alsterpaullone, GSK3B inhibitor VIII, GSK3B inhibitor XV, Indirubin 3'-monoxime, L glutathione reduced, Fluocinolone acetonide, Tirofiban, Topotecan hydrochloride, Clofarabine, Vinblastine, Menadione Crystalline and derivatives or analogues thereof.

The present invention also relates to a compound selected from the group consisting of Gemcitabine, Obatoclax Mesylate, Docetaxel, HA-14, Alsterpaullone, GSK3B inhibitor VIII, GSK3B inhibitor XV, Indirubin 3'-monoxime, L glutathione reduced, Fluocinolone acetonide, Tirofiban, Topotecan hydrochloride, Clofarabine, Vinblastine, Menadione Crystalline and derivatives or analogues thereof for use in the treatment of a, influenza infection in a subject in need thereof.

DETAILED DESCRIPTION OF THE INVENTION

The inventors have now identified different compounds that inhibit the replication of influenza virus, and that can be used as drugs for treating influenza infections. Said compounds are depicted in Table 1 and are known per se by the skilled man in the art:

| Name | FDA status | IUPAC name |
|---|---|---|
| Alsterpaullone | NonApproved | 14-nitro-8,18-diazatetracyclo[9.7.0.0^{2,7}.0^{12,17}]octadeca-1(11),2(7),3,5,12(17),13,15-heptaen-9-one |
| Vinblastine | Approved | methyl (1R,9R,10S,11R,12R,19R)-11-(acetyloxy)-12-ethyl-4-[(13S,15S,17S)-17-ethyl-17-hydroxy-13-(methoxycarbonyl)-1,11-diazatetracyclo[13.3.1.0^{4,12}.0^{5,10}]nonadeca-4(12),5(10),6,8-tetraen-13-yl]-10-hydroxy-5-methoxy-8-methyl-8,16-diazapentacyclo[10.6.1.0^{1,9}.0^{2,7}.0^{16,19}]nonadeca-2(7),3,5,13-tetraene-10-carboxylate |
| Menadione Crystalline | Approved | 2-methyl-1,4-dihydronaphthalene-1,4-dione |
| GSK inhibitor VIII | NonApproved | N-(4-Methoxybenzyl)-N'-(5-nitro-1,3-thiazol-2-yl)urea |
| Gemcitabine | Approved | 4-amino-1-[(2R,4R,5R)-3,3-difluoro-4-hydroxy-5-(hydroxymethyl)oxolan-2-yl]-1,2-dihydropyrimidin-2-one |
| GSK-3 inhibitor XV | NonApproved | pyridocarbazolo-cyclopentadienyl Ruthenium complex, racemic mixture |
| Docetaxel | Approved | (1S,2S,3R,4S,7R,9S,10S,12R,15S)-4-(acetyloxy)-15-{[(2R,3S)-3-{[(tert-butoxy)carbonyl]amino}-2-hydroxy-3-phenylpropanoyl]oxy}-1,9,12-trihydroxy-10,14,17,17-tetramethyl-11-oxo-6-oxatetracyclo[11.3.1.0^{3,10}.0^{4,7}]heptadec-13-en-2-yl benzoate |
| Obatoclax mesylate (GX15-07) | NonApproved | (2E)-2-[(5E)-5-[(3,5-dimethyl-1H-pyrrol-2-yl)methylidene]-4-methoxypyrrol-2-ylidene]indole; methanesulfonic acid |
| Indirubin-3'-Monoxime | NonApproved | 3-[(3E)-3-(hydroxyimino)-2,3-dihydro-1H-indol-2-ylidene]-2,3-dihydro-1H-indol-2-one |
| fluocinolone acetonide | Approved | (1S,2S,4R,8S,9S,11S,12R,13S,19S)-12,19-difluoro-11-hydroxy-8-(2-hydroxyacetyl)-6,6,9,13-tetramethyl-5,7-dioxapentacyclo[10.8.0.0^{2,9}.0^{4,8}.0^{13,18}]icosa-14,17-dien-16-one |
| L-Glutathione reduced | Approved | (2S)-2-amino-4-{[(1R)-1-[(carboxymethyl)carbamoyl]-2-sulfanylethyl]carbamoyl}butanoic acid |
| Tirofiban | Approved | (2S)-2-(butane-1-sulfonamido)-3-{4-[4-(piperidin-4-yl)butoxy]phenyl}propanoic acid |
| HA-14 | NonApproved | Ethyl [2-amino-6-bromo-4-(1-cyano-2-ethoxy-2-oxoethyl)]-4H-chromene-3-carboxylate |
| Topotecan hydrochloride | Approved | (19S)-8-[(dimethylamino)methyl]-19-ethyl-7,19-dihydroxy-17-oxa-3,13-diazapentacyclo[11.8.0.0^{2,11}.0^{4,9}.0^{15,20}]henicosa-1(21),2,4(9),5,7,10,15(20)-heptaene-14,18-dione |
| Clofarabine | Approved | (2R,3R,4S,5R)-5-(6-amino-2-chloro-9H-purin-9-yl)-4-fluoro-2-(hydroxymethyl)oxolan-3-ol |

Accordingly, the present invention relates to a method for inhibiting the replication capacity of an influenza virus in an infected cell comprising the steps consisting contacting said infected cell with a least one compound selected from the group consisting of Gemcitabine, Obatoclax Mesylate, Docetaxel, HA-14, Alsterpaullone, GSK3B inhibitor VIII, GSK3B inhibitor XV, Indirubin 3'-monoxime, L glutathione reduced, Fluocinolone acetonide, Tirofiban, Topotecan hydrochloride, Clofarabine, Vinblastine, Menadione Crystalline and derivatives or analogues thereof.

The term "inhibiting the replication capacity," as used herein with reference to a viral phenotype, means that the virus grows to a lower titer in the presence of a compound as above described relative to the virus grown in the absence of said compound. In one embodiment, the presence of said compound which will inhibit the ability of an influenza virus to replicate in a human cell by at least about 10%, or by at least about 20%, or by at least about 30%, or by at least about 40%, or by at least about 50%, or by at least about 60%, or by at least about 70%, or by at least about 80%, or by at least about 90%, or by at least about 100%, or by at least about 200%, or by at least about 300%, or by at least about 400%, or by at least about 500% when compared to said influenza virus grown in the absence of said compound.

According to the invention, said infected cell is a eukaryotic infected cell including avian and mammalian cells. Preferably said infected cell is a mammalian cell. Typically said mammalian cells include but are not limited to cells from humans, cats, cattle, horses, sheep, pigs, goats, and rabbits.

The present invention also relates to a compound selected from the group consisting of Gemcitabine, Obatoclax Mesylate, Docetaxel, HA-14, Alsterpaullone, GSK3B inhibitor VIII, GSK3B inhibitor XV, Indirubin 3'-monoxime, L glutathione reduced, Fluocinolone acetonide, Tirofiban, Topotecan hydrochloride, Clofarabine, Vinblastine, Menadione Crystalline and derivatives or analogues thereof for use in the treatment of a, influenza infection in a subject in need thereof As used herein, the term "influenza infection" has its general meaning in the art and refers to the disease caused by an infection with an influenza virus. In some embodiments of the invention, influenza infection is associated with Influenza virus A or B. In some embodiments of the invention, influenza infection is associated with Influenza virus A. In some specific embodiments of the invention, influenza infection is cause by influenza virus A that is H1N1, H2N2, H3N2 or H5N1.

The subject can be human or any other animal (e.g., birds and mammals) susceptible to influenza infection (e.g. domestic animals such as cats and dogs; livestock and farm animals such as horses, cows, pigs, chickens, etc.). Typically said subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant.

For example, therapeutic treatments includes the reduction or amelioration of the progression, severity and/or duration of influenza infections, or the amelioration of one or more symptoms (specifically, one or more discernible symptoms) of influenza infections, resulting from the administration of at least one compound of the invention. In specific embodiments, the therapeutic treatment includes the amelioration of at least one measurable physical parameter of an influenza infection. In other embodiments the therapeutic treatment includes the inhibition of the progression of an influenza infection, either physically by, e.g., stabilization of a discernible symptom, physiologically by, e.g., stabilization of a physical parameter, or both. In other embodiments the therapeutic treatment includes the reduction or stabilization of influenza infections. Antiviral drugs can be used in the community setting to treat people who already have influenza to reduce the severity of symptoms and reduce the number of days that they are sick.

In a particular embodiment, the compounds of the invention may be used in a prophylactic treatment. The terms "prophylaxis" or "prophylactic use" and "prophylactic treatment" as used herein, refer to any medical or public health procedure whose purpose is to prevent, rather than treat or cure a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a subject with the disease.

As used herein, prophylactic use includes the use in situations in which an outbreak has been detected, to prevent contagion or spread of the infection in places where a lot of people that are at high risk of serious influenza complications live in close contact with each other (e.g. in a hospital ward, daycare center, prison, nursing home, etc). It also includes the use among populations who require protection from the influenza but who either do not get protection after vaccination (e.g. due to weak immune system), or when the vaccine is unavailable to them, or when they cannot get the vaccine because of side effects. It also includes use during the two weeks following vaccination, since during that time the vaccine is still ineffective. Prophylactic use may also include treating a person who is not ill with the influenza or not considered at high risk for complications, in order to reduce the chances of getting infected with the influenza and passing it on to a high-risk person in close contact with him (for instance, healthcare workers, nursing home workers, etc).

Typically, the compounds of the invention are administered to the subject in a effective amount. As used herein, an "effective amount" refers to an amount sufficient to elicit the desired biological response. In the present invention the desired biological response is to inhibit the replication of influenza virus, to reduce the amount of influenza viruses or to reduce or ameliorate the severity, duration, progression, or onset of a influenza virus infection, prevent the advancement of an influenza viruses infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti viral agents, e.g., when coadministered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between approximately 0.01 to 100 mg/kg body weight/day for therapeutic or prophylactic treatment.

Generally, dosage regimens can be selected in accordance with a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

Dosages of the compounds described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), tree times a day (e.g., every 8 hours), or four times a day (e.g., every 6 hours).

For therapeutic treatment, the compounds described herein can be administered to a subject within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc.

For prophylactic treatment during a community outbreak, the compounds described herein can be administered to a subject within, for example, 2 days of onset of symptoms in the index case, and can be continued for any suitable duration, for example, for 7 days, 10 days, 14 days, 20 days, 28 days, 35 days, 42 days, etc.

Various types of administration methods can be employed in the invention, and are described in detail below.

In a particular embodiment the compounds of the invention are use in combination with an additional suitable therapeutic agent, for example, an antiviral agent or a vaccine. When "combination therapy" is employed, an effective amount can be achieved using a first amount of a compound of the invention and a second amount of an additional suitable therapeutic agent (e.g. an antiviral agent or vaccine).

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

Specific examples that can be co-administered with a compound of the invention include neuraminidase inhibitors. Examples of neuraminidase inhibitors include oseltamivir, oseltamivir carboxylate (GS4071; see e.g. Eisenberg et al., Antimicrob Agents Chemother. (1997) 41:1949-52), zanamivir, peramivir (RWJ-27021; BXC-1812, BioCryst), 2,3-didehydro-2-deoxy-N-acetylneuraminic acid (DANA), 2-deoxy-2,3-dehydro-N-trifluoroacetylneuraminic acid (FANA), A-322278, and A-315675 (see U.S. Pat. No. 6,455, 571 to Maring et al, and Kati et al., Antimicrob Agents Chemother. (2002) 46:1014-21).

Specific examples that can be co-administered with a compound of the invention include M2 inhibitors. Examples of M2 inhibitors include include aminoadamantane compounds such as amantadine (1-amino-adamantane), rimantadine (1-(1-aminoethyl)adamantane), spiro[cyclopropane-1,2'-adamantan]-2-amine, spiro[pyrrolidine-2,2'-adamantane], spiro [piperidine-2,2'-adamantane], 2-(2-adamantyl)piperidine, 3-(2-adamantyl)pyrrolidine, 2-(1-adamantyl) piperidine, 2-(1-adamantyl)pyrrolidine, and 2-(ladamantyl)-2-methyl-pyrrolidine; and M2-specific monoclonal antibodies (see e.g. US 20050170334; and Zebedee and Lamb, J. Virol. (1988) 62:2762-72).

Specific examples that can be co-administered with a compound of the invention include RNA polymerase inhibitors. As used herein, the term RNA polymerase inhibitor refers to an antiviral agent that inhibits the polymerase, protease, and/or endonuclease activity of the viral RNA polymerase complex or one of its subunits (i.e. PB1, PB2andPA). Exemplary RNA polymerase inhibitors include antiviral nucleoside analogs such as ribavirin, viramidine, 6-fluoro-3-hydroxy-2pyrazinecarboxamide (T-705), 2'-deoxy-2'-fluoroguanosine, pyrazofurin, 3-deazaguanine, carbodine (see e.g. Shannon et al., Antimicrob Agents Chemother. (1981) 20:769-76), and cyclopenenyl cytosine (see e.g. Shigeta et al., Antimicrob Agents Chemother. (1988) 32:906-11); and the endonuclease inhibitor flutimide (see e.g. Tomassini et al., Antimicrob Agents Chemother. (1996) 40:1189-93).

Specific examples that can be co-administered with a compound of the invention include influenza-specific interfering oligonucleotides Examples of influenza-specific interfering oligonucleotides include siRNAs (see e.g. Zhou et al., Antiviral Res. (2007) 76:186-93), antisense oligonucleotides, phosphorothioate oligonucleotides, ribozymes (see e.g. U.S. Pat. No. 6,258,585 to Draper), morpholino oligomers and peptide nucleic acids (see e.g. Schubert and Kurreck, Handb Exp Pharmacol. (2006) 173:261-87).

Specific examples that can be co-administered with a compound of the invention include interferons. An "interferon" or "IFN", as used herein, is intended to include any molecule defined as such in the literature, comprising for example any types of IFNs (type I and type II) and in particular, IFN-alpha, IFN-beta, INF-omega and IFN-gamma. The term interferon, as used herein, is also intended to encompass salts, functional derivatives, variants, muteins, fused proteins, analogs and active fragments thereof. In a preferred embodiment the interferon is interferon-alpha. Interferon-alpha includes, but is not limited to, recombinant interferon-α2a (such as ROFERON® interferon available from Hoffman-LaRoche, Nutley, N.J.), interferon-α2b (such as Intron-A interferon available from Schering Corp., Kenilworth, N.J., USA), a consensus interferon, and a purified interferon-α product.

In some embodiments, the compounds described herein can be co-administered with an influenza vaccine. Influenza vaccines, of all kinds, are usually trivalent vaccines. They generally contain antigens derived from two influenza A virus strains and one influenza B strain. A standard 0.5 ml injectable dose in most cases contains 15 ug of hemagglutinin antigen component from each strain, as measured by single radial immunodiffusion (SRD). The influenza virus strains to be incorporated into influenza vaccine each season are determined by the World Health Organization in collaboration with national health authorities and vaccine manufacturers.

In some embodiments, a combination therapy comprises active immunization with an influenza antigenic polypeptide (e.g. influenza hemagglutinin and the matrix 2 ectodomain polypeptides) or passive immunization with one or more neutralizing antibodies directed to an influenza antigenic polypeptide (e.g. antibodies raised against the influenza hemagglutinin and the matrix 2 ectodomain polypeptides).

The compounds of the invention can be formulated into pharmaceutical compositions that further comprise a pharmaceutically acceptable carrier, diluent, adjuvant or vehicle. In one embodiment, the present invention relates to a pharmaceutical composition comprising a compound of the invention described above, and a pharmaceutically acceptable carrier, diluent, adjuvant or vehicle. In one embodiment, the present invention is a pharmaceutical composition comprising an effective amount of a compound of the present invention or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions described herein may be administered orally, parenterally, by inhalation spray, topically, rectally, nasally, buccally, vaginally or via an implanted reservoir depending on the severity of the infection being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered to the respiratory tract. The respiratory tract includes the upper airways, including the oropharynx and larynx, followed by the lower airways, which include the trachea followed by bifurcations into the bronchi and bronchioli. Pulmonary delivery compositions can be delivered by inhalation by the patient of a dispersion so that the active ingredient within the dispersion can reach the lung where it can, for example, be readily absorbed through the alveolar region directly into blood circulation. Pulmonary delivery can be achieved by different approaches, including the use of nebulized, aerosolized, micellular and dry powder-based formulations; administration by inhalation may be oral and/or nasal. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self contained. Dry powder dispersion devices, for example, deliver drugs that may be readily formulated as dry powders. A pharmaceutical composition of the invention may be stably stored as lyophilized or spray-dried powders by itself or in combination with suitable powder carriers. The delivery of a pharmaceutical composition of the invention for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament. Examples of pharmaceutical devices for aerosol delivery include metered dose inhalers (MDIs), dry powder inhalers (DPIs), and air-jet nebulizers.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

The invention will be further illustrated by the following figures and examples. However, these examples and figures should not be interpreted in any way as limiting the scope of the present invention.

FIGURES

FIG. 1: MDCK or A549 cells were treated with increasing concentrations of Gemcitabine (Δ), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 2:
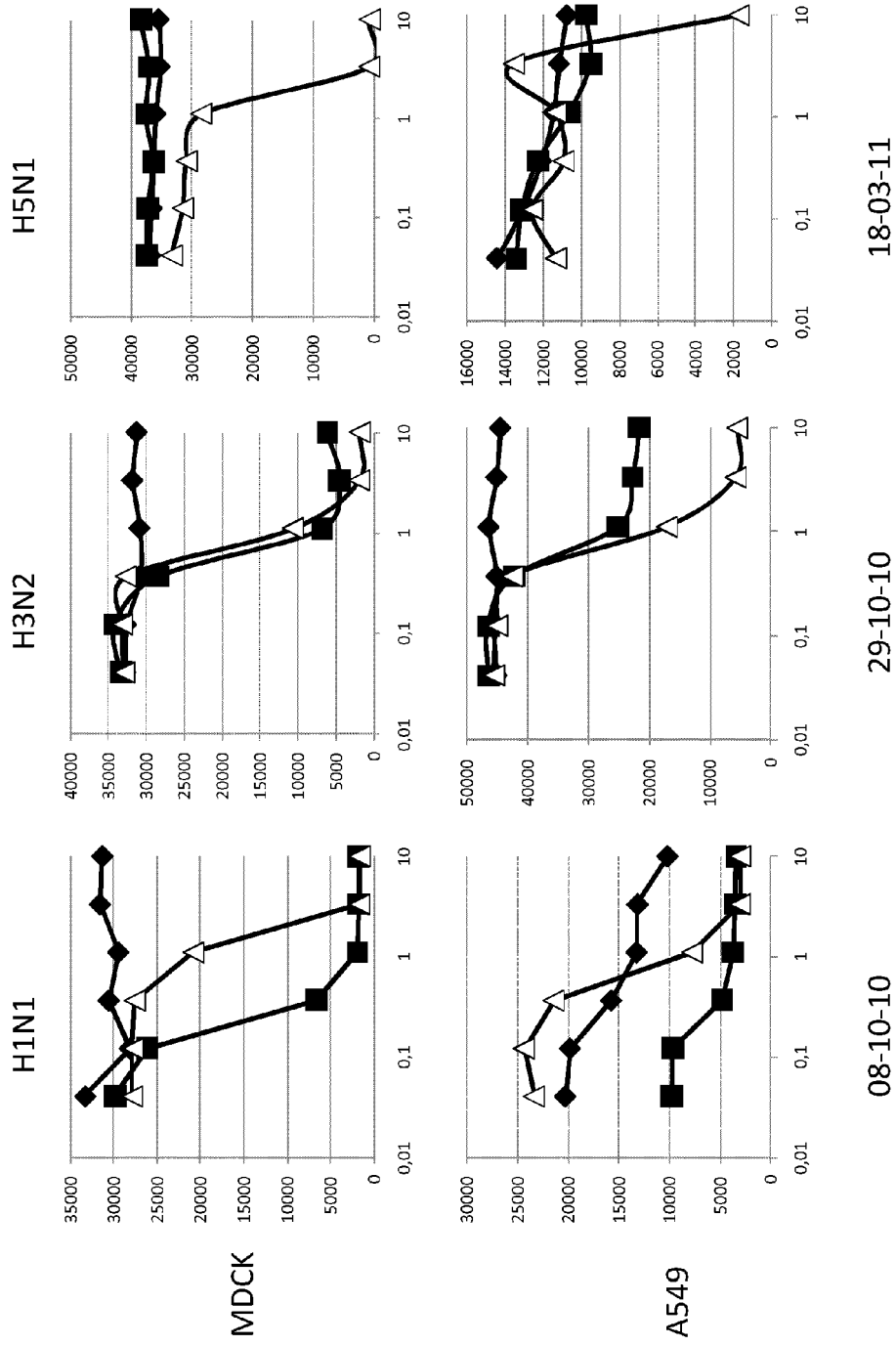

FIG. 2: MDCK or A549 cells were treated with increasing concentrations of Alsterpaullone (Δ), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 3:
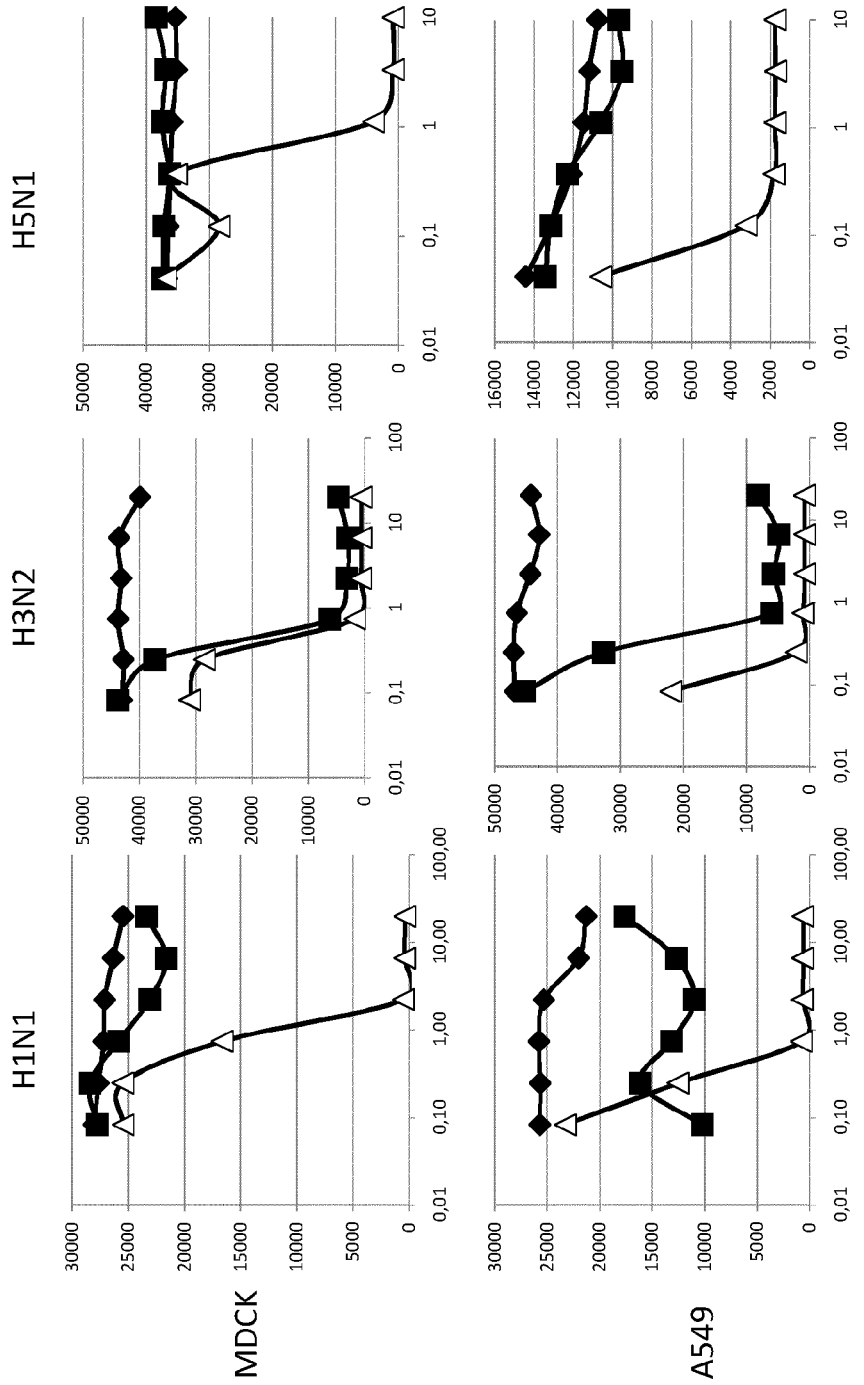

FIG. 3: MDCK or A549 cells were treated with increasing concentrations of Obatoclax mesylate (Δ), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 4:
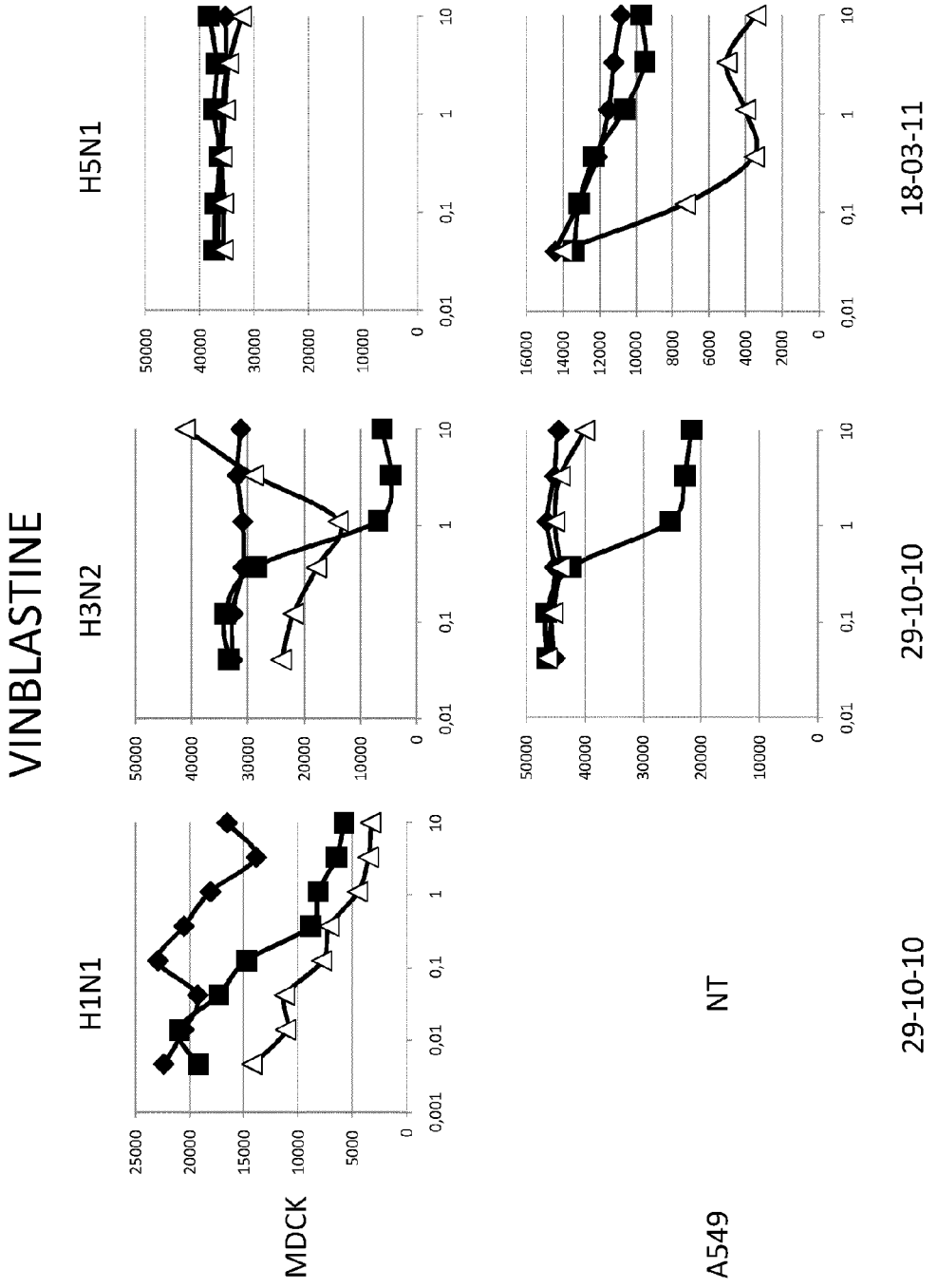

FIG. 4: MDCK or A549 cells were treated with increasing concentrations of Vinblastine (Δ), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 5:
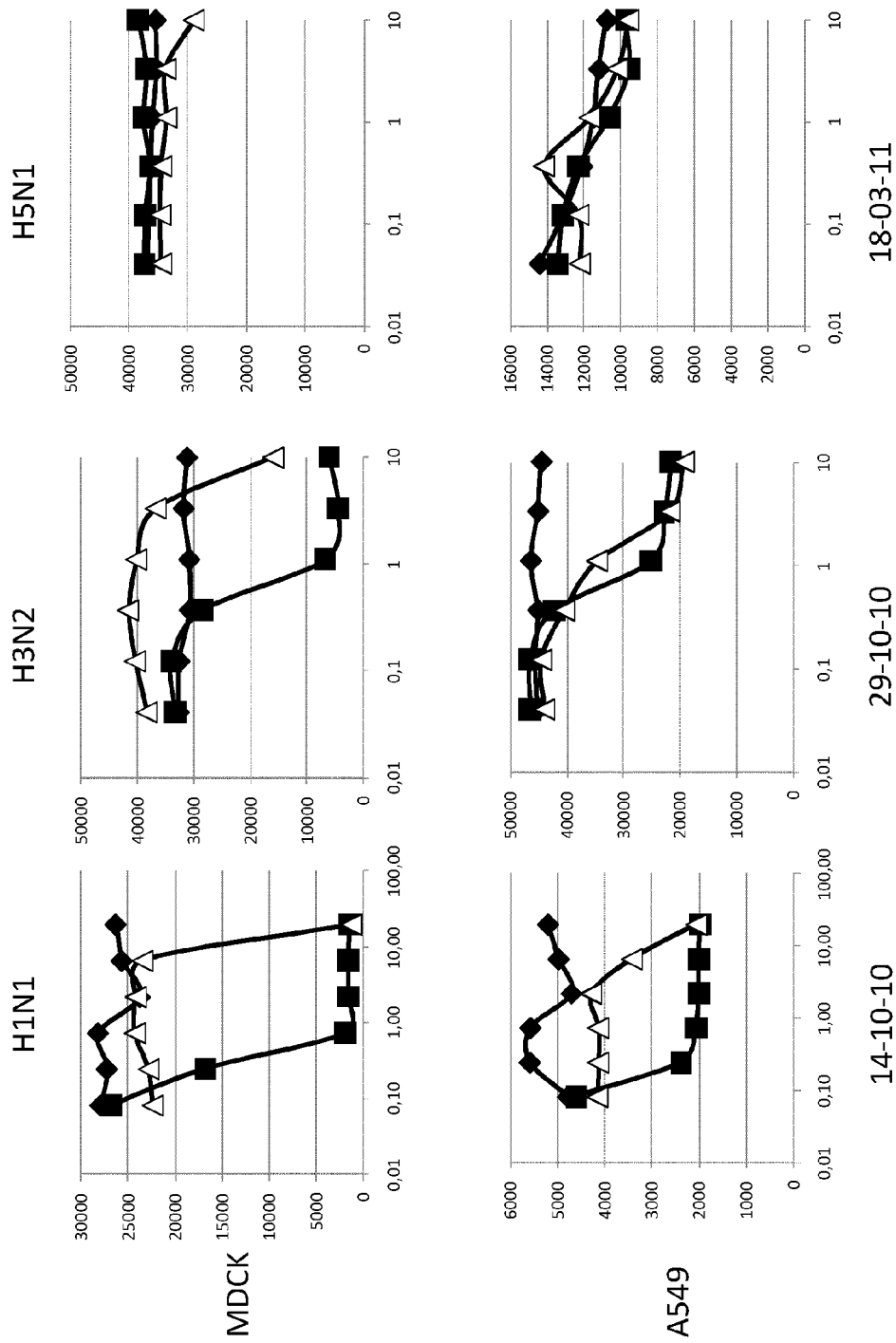

FIG. 5: MDCK or A549 cells were treated with increasing concentrations of Menadione Crystalline (Δ), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 6:
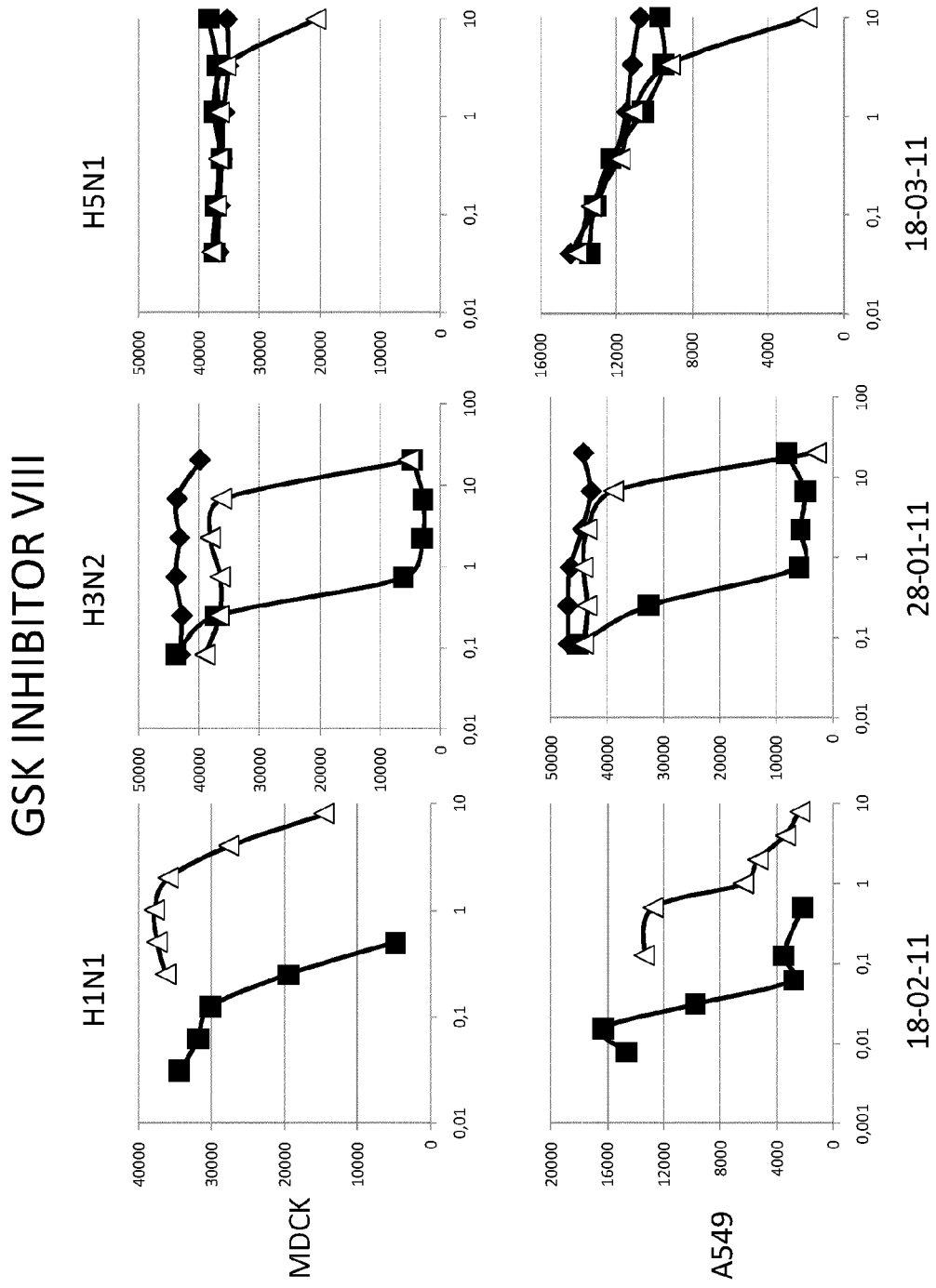

FIG. 6: MDCK or A549 cells were treated with increasing concentrations of GSK Inhibitor VIII (Δ), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 7:
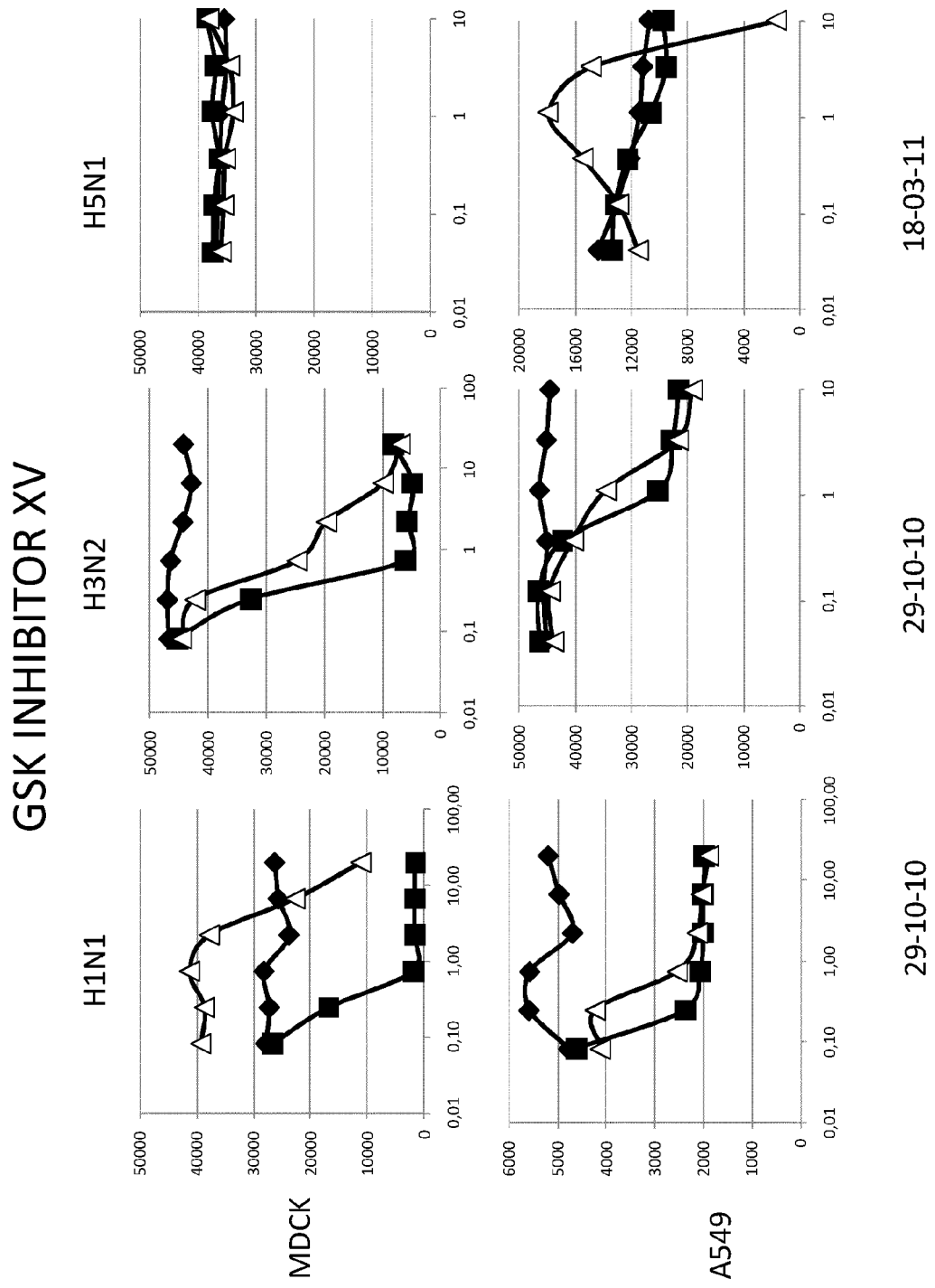

FIG. 7: MDCK or A549 cells were treated with increasing concentrations of GSK Inhibitor XV (Δ), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 8:
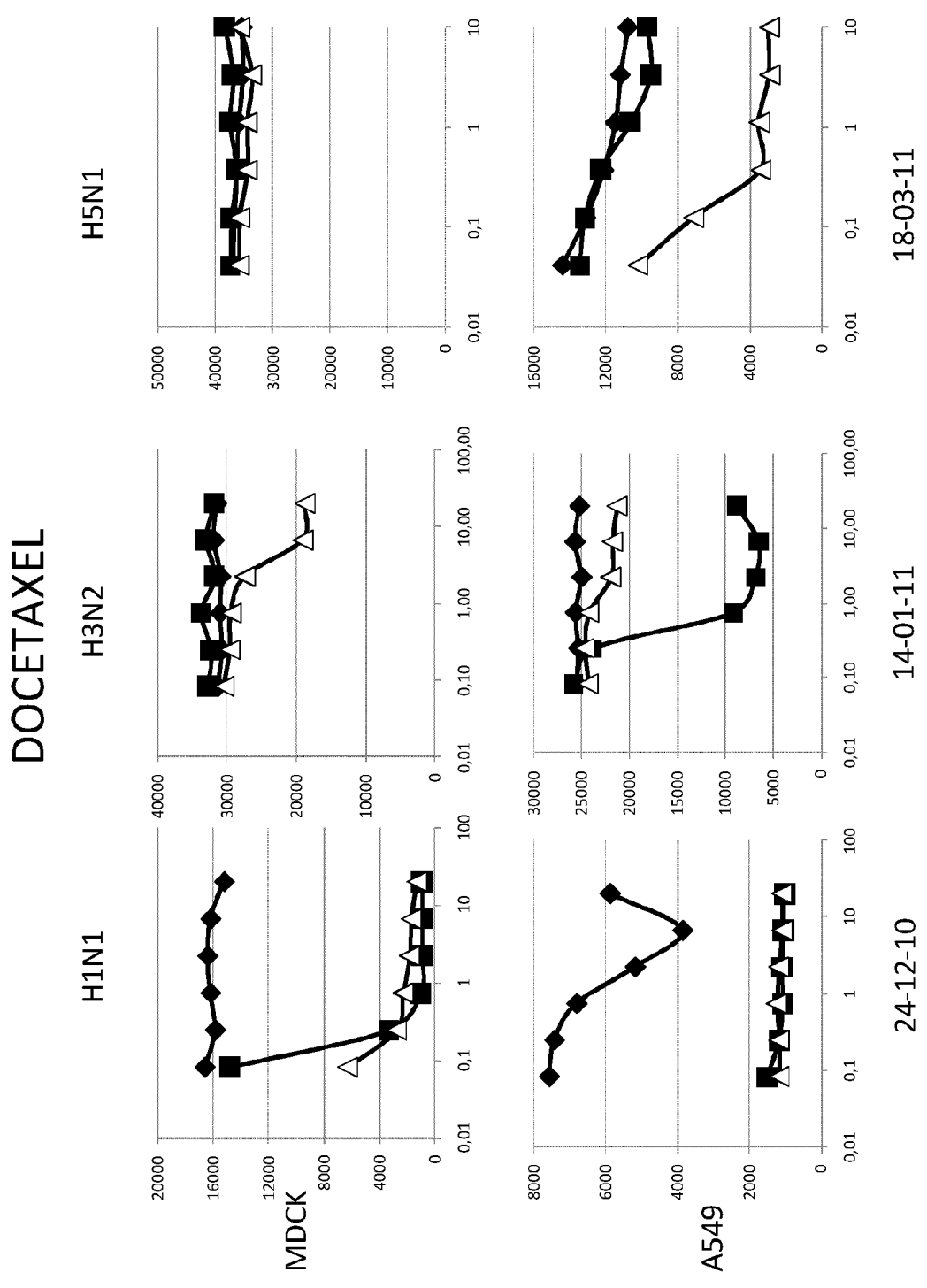

FIG. 8: MDCK or A549 cells were treated with increasing concentrations of Docetaxel (Δ), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 9:
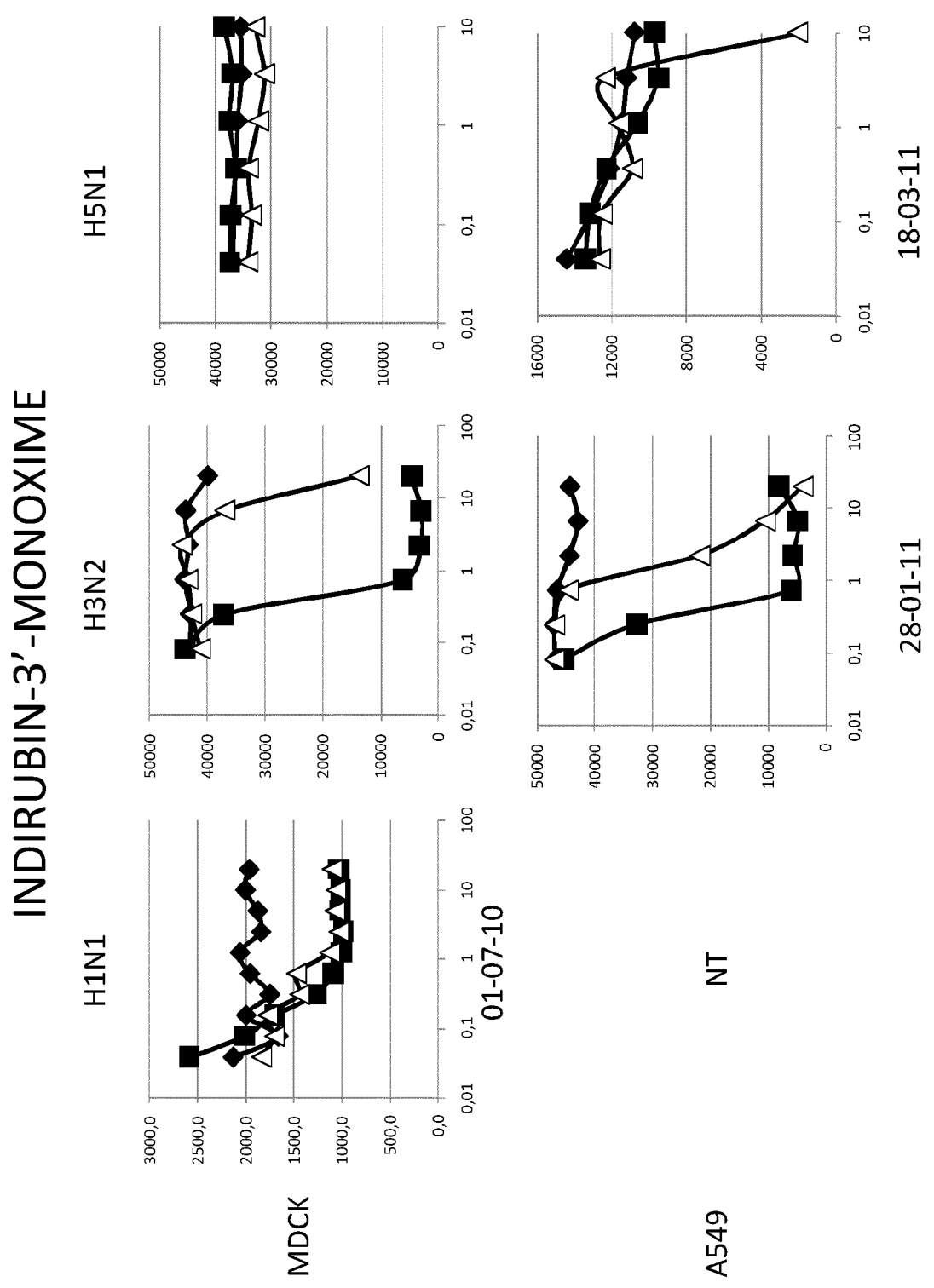

FIG. 9: MDCK or A549 cells were treated with increasing concentrations of indirubin-3'-monoxime (A), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 10:
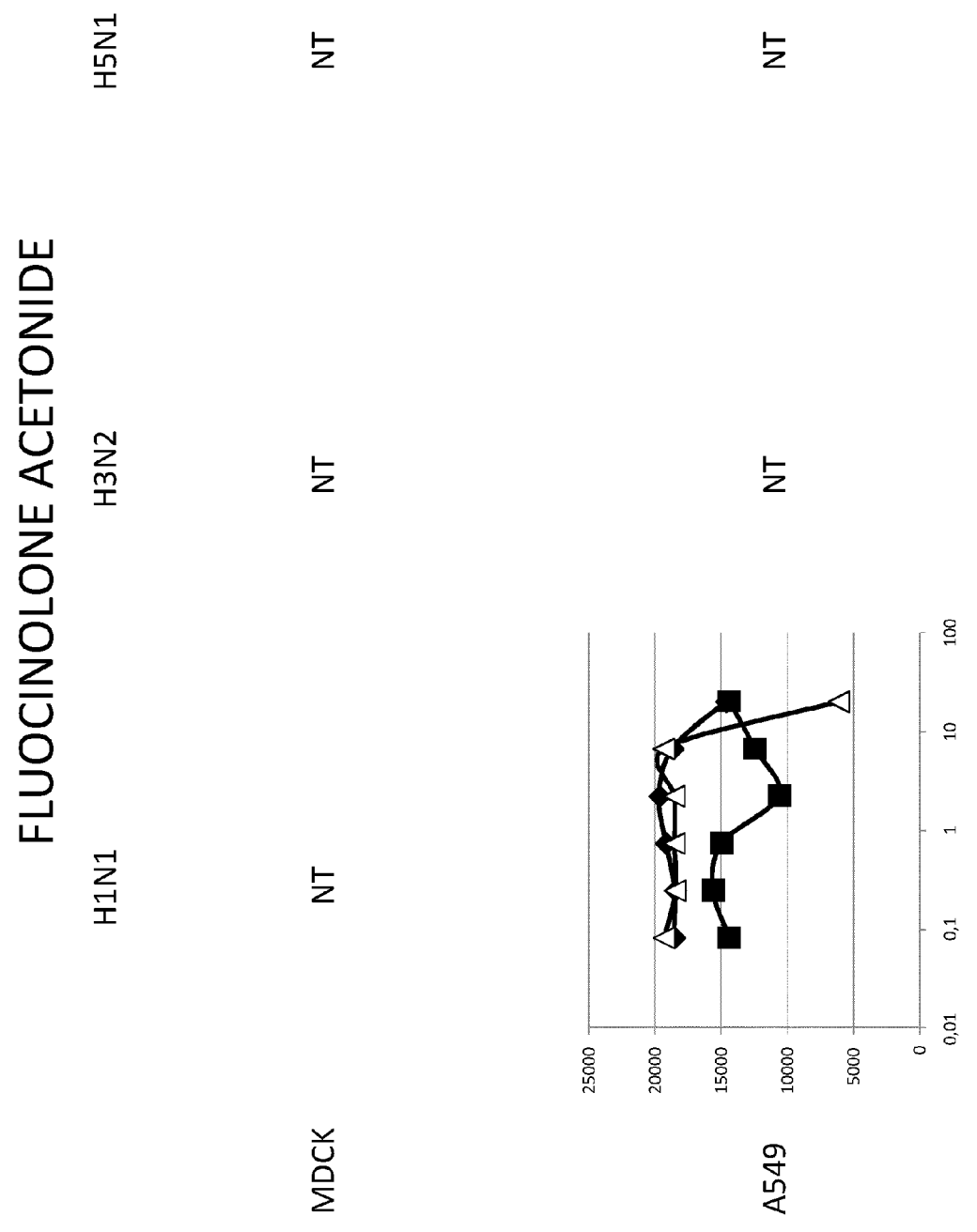

FIG. 10: MDCK or A549 cells were treated with increasing concentrations of Fluocinolone Acetonide (A), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 11:
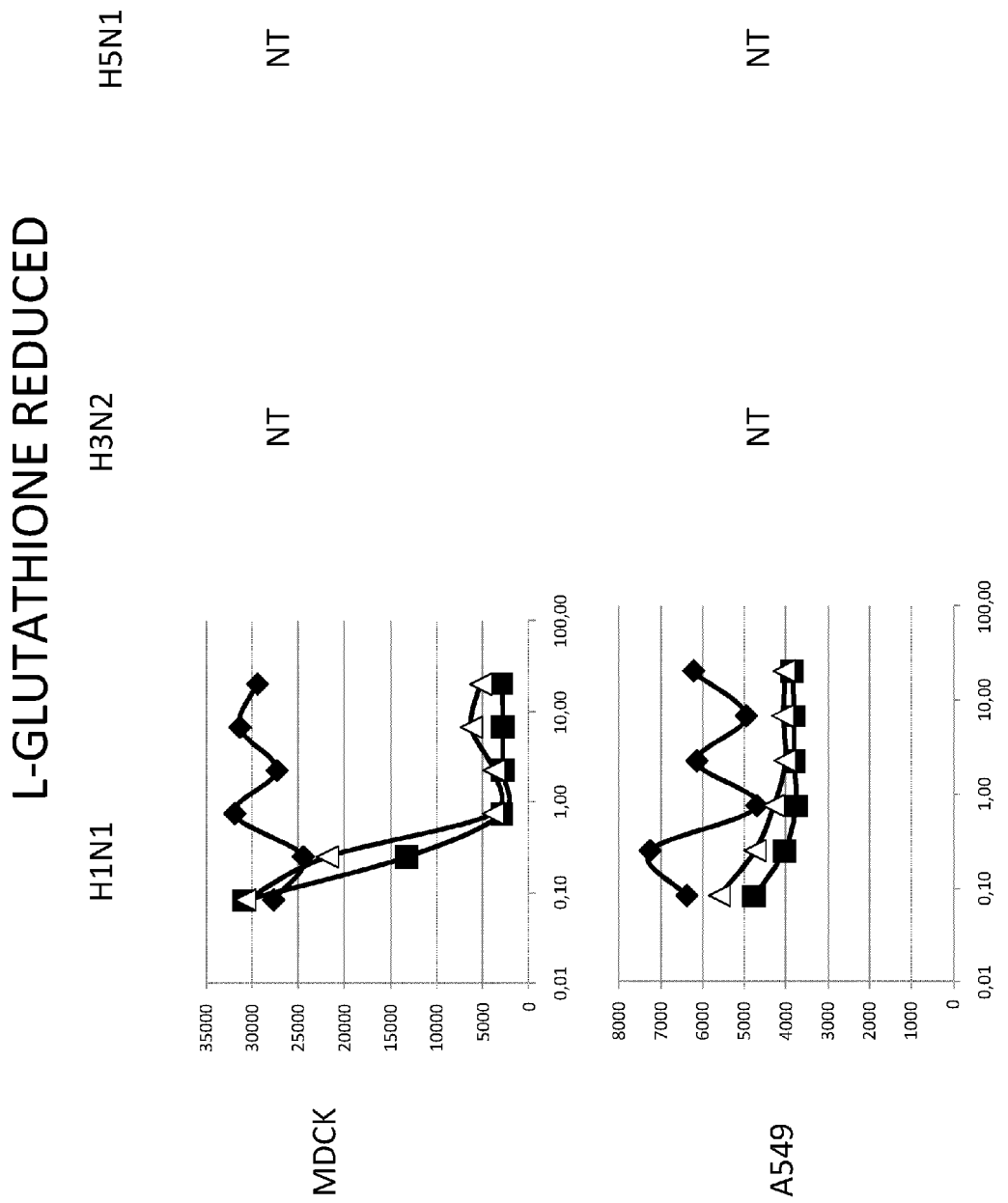

FIG. 11: MDCK or A549 cells were treated with increasing concentrations of L-Guthatione Reduced (A), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 12:
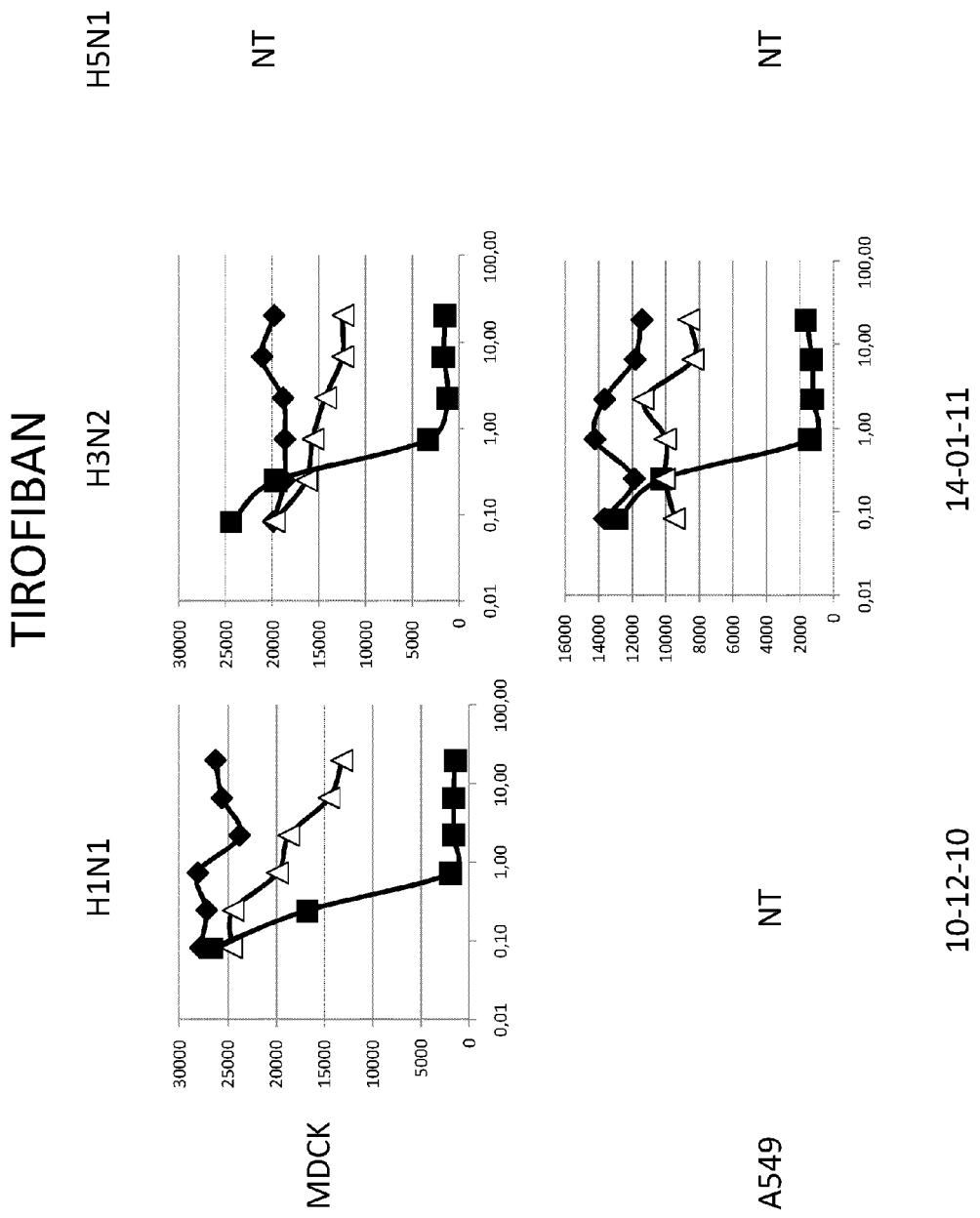

FIG. 12: MDCK or A549 cells were treated with increasing concentrations of Tirofiban (A), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 13:
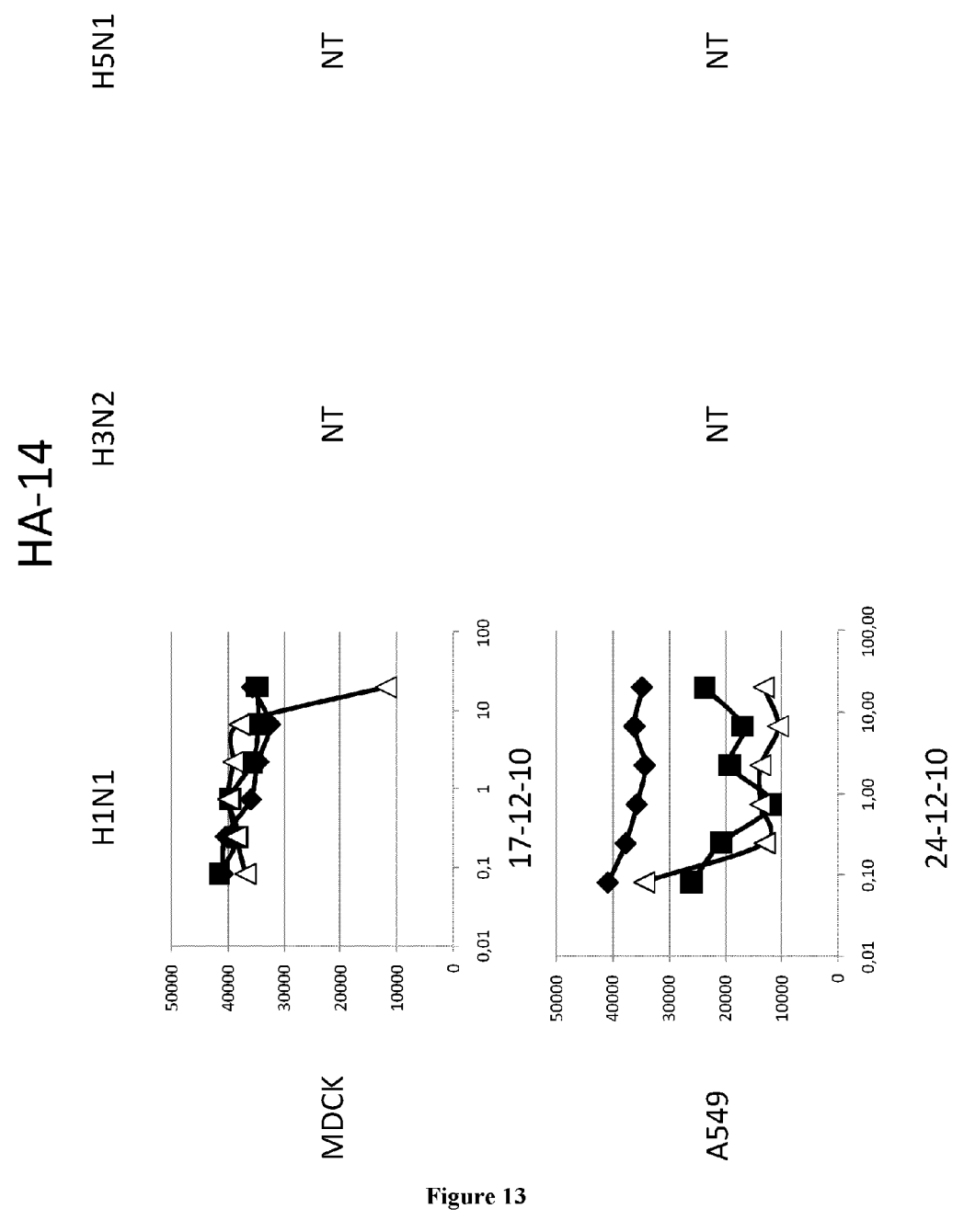

FIG. 13: MDCK or A549 cells were treated with increasing concentrations of HA-14 (A), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 14:
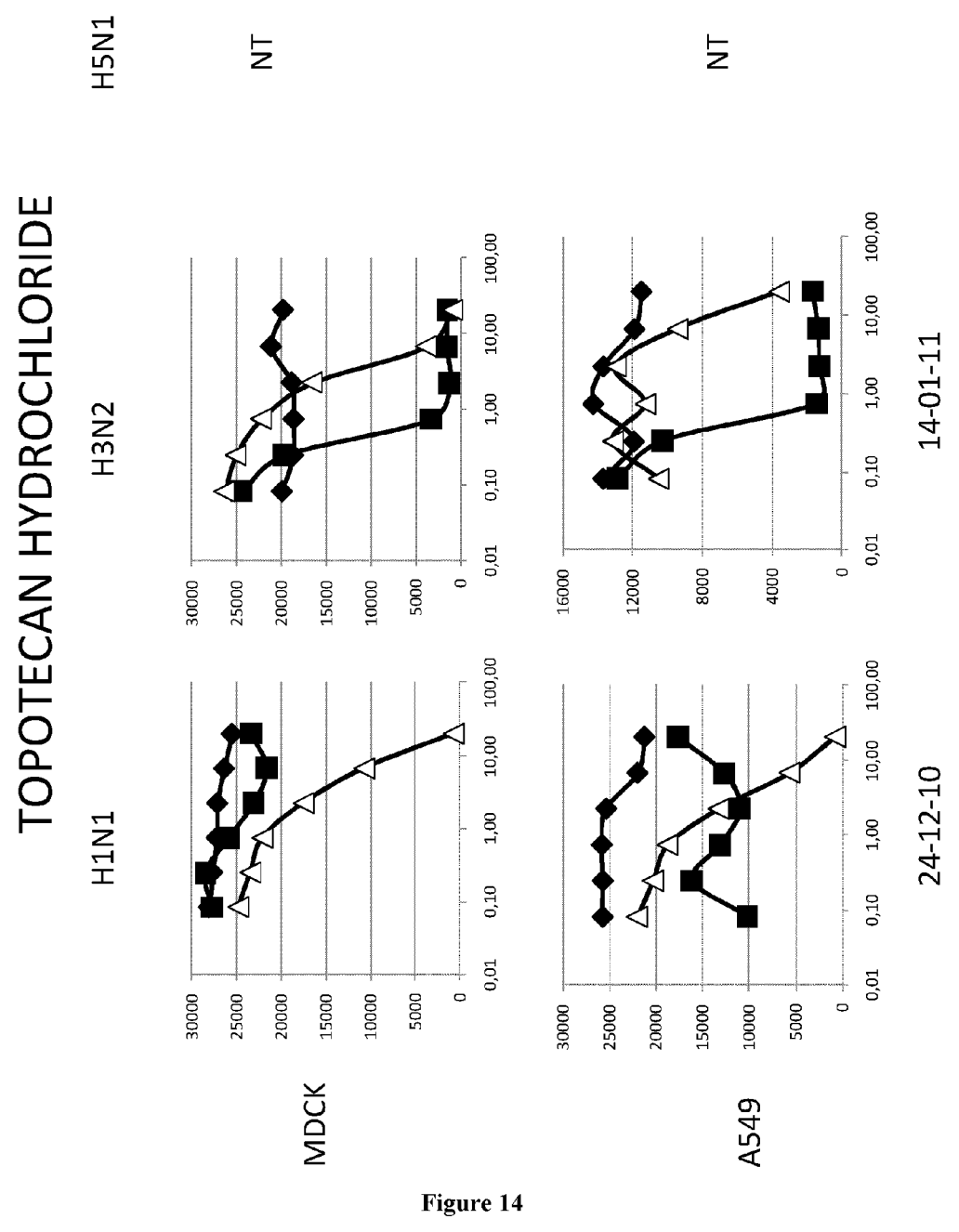

FIG. 14: MDCK or A549 cells were treated with increasing concentrations of Topotecan Hydrochloride (A), Amantadine (antiviral molecule control) (■) or DMSO (♦) Immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

Figure 15:
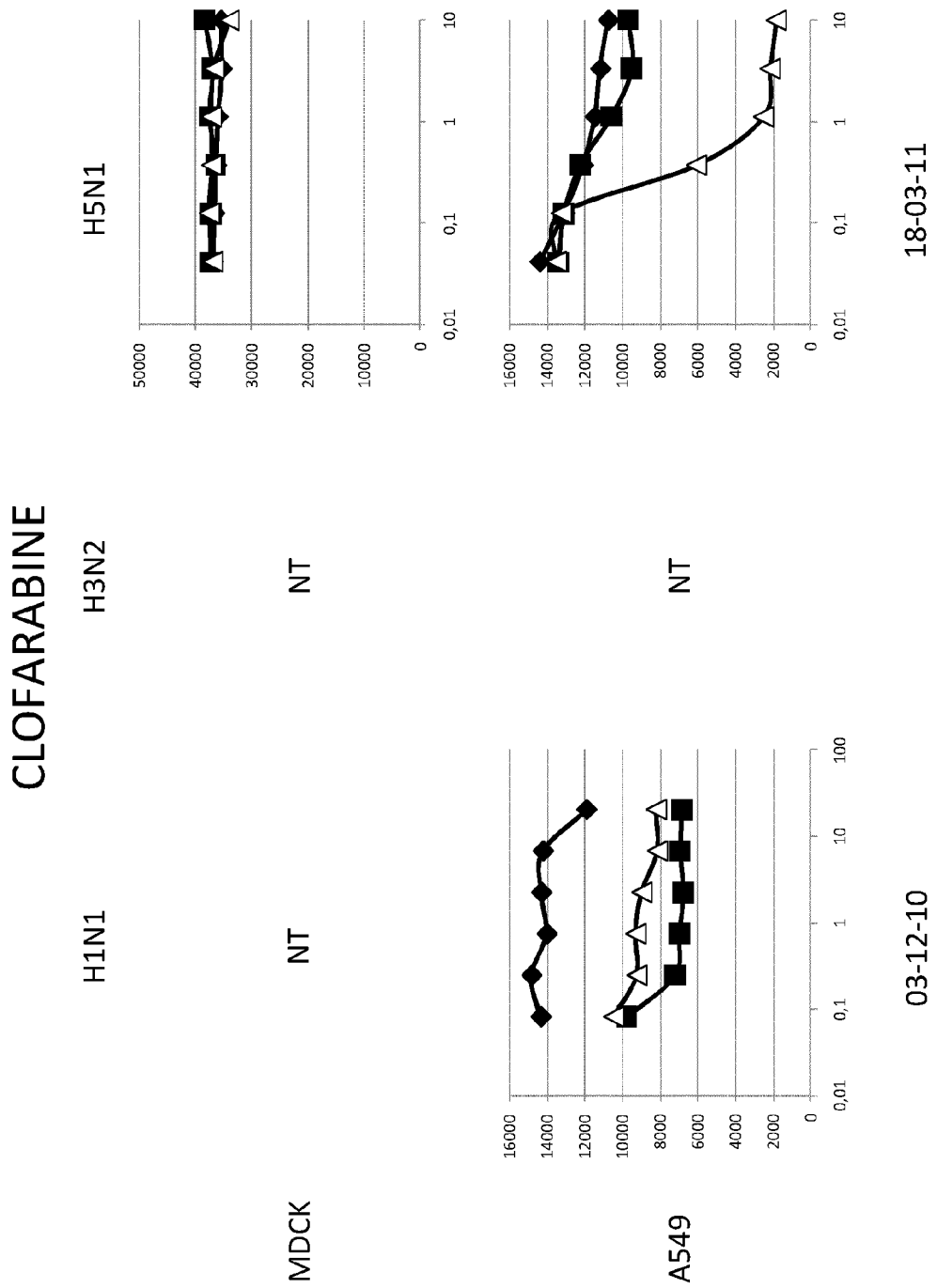

FIG. 15: MDCK or A549 cells were treated with increasing concentrations of Clofarabine (A), Amantadine (antiviral molecule control) (■) or DMSO (♦) immediately before infection with H1N1 (respectively MOI 0.01 or MOI 0.1), H3N2 (MOI 0.6) or H5N1 (respectively MOI 0.001 or MOI 0.01). 24 h and 48 h post infection, supernatants were harvested and tested for the neuraminidase activity using a fluorometric assay. Fluorescence curves are given showing the effect of molecules on viral replication.

EXAMPLE

Material & Methods

Cells and Virus

The A549 human lung epithelial cells line and the Madin-Darby canine kidney cells (ECACC,) were grown in DMEM media (GibCo, 41966052) supplemented with 100 U.ml penicilline/streptomycin (GibCo, 15140130) and 10% fetal calf serum (PAN, 3302-P221126) at 37° C. and 5%CO2.

The epidemic A/H1N1/New Caledonia/P10, A/H3N2/Wyoming and A/H5N1/Vietnam strains were propagated in MDCK cells in DMEM supplemented with 1 µg.ml$^{-1}$ modified trypsin TPCK (Sigma, T3053) in absence of FCS. Virus stocks were titrated by standard plaque assay on MDCK cells using an agar overlay medium.

Molecules

All the molecules were solubilized in DMSO at a stock concentration of 20 mM.

Virus Infection

Cells (MDCK or A549) were washed twice with D-PBS 1X (GibCo, 14190). Molecules were added at indicated concentrations. MDCK and A549 cells were then infected with H1N1 (respectively MOI 0.01 and 0.1), with H3N2 (MOI 0.6) or with H5N1 (respectively MOI 0.001 and 0.01) in DMEM supplemented with 0.2 µg.ml$^{-1}$ trypsin TPCK (infection medium) and incubated for 24 h or 48 h in infection medium at 37° C. and 5% $CO_2$.

Titer Measure by Neuraminidase Activity

Influenza virus neuraminidase is able to cleave the methyl-umbelliferyl-N-acetylneuraminic acid (4-MUNANA, Sigma M8639) modifying its emission wavelength in a dose-dependent manner.

In 96-black plate (Corning, 3631), 25 µl infection supernatants were diluted in 25 µl D-PBS1X containing calcium and magnesium (GibCo, 14040) and 50 µl of 20 µM 4-MUNANA. After 1 h incubation at 37° C., 100 µl of glycine 0.1 M 25% ethanol pH10.7 was added. Measures were done with TECAN infinite M1000 instrument at 365 nm excitation wavelength and 450 nm emission wavelength.

Results

All the results are depicted in FIGS. 1-15.

REFERENCES

Throughout this application, various references describe the state of the art to which this invention pertains. The disclosures of these references are hereby incorporated by reference into the present disclosure.

The invention claimed is:

1. A method for the treatment of an influenza infection in a subject infected by influenza virus comprising administering to the subject an effective amount of Obatoclax Mesylate.

2. The method according to claim 1 wherein the subject is a human.

3. The method according to claim 1, wherein the compound is administered to the subject in combination with an additional suitable therapeutic agent selected from the group consisting of neuraminidase inhibitors, M2 inhibitors, RNA polymerase inhibitors, interferons, influenza vaccine, influenza antigenic polypeptides and neutralizing antibodies directed to an influenza antigenic polypeptide.

4. The method according to claim 1, wherein said compound is administered to the respiratory tract of said subject.

5. The method according to 1 wherein the influenza virus is selected from the group consisting of H1N1, H2N2, H3N2, and H5N1.

6. The method according to claim 2 wherein the influenza virus is selected from the group consisting of H1N1, H2N2, H3N2, and H5N1.

7. The method according to claim 3 wherein the influenza virus is selected from the group consisting of H1N1, H2N2, H3N2, and H5N1.

8. The method according to claim 2 wherein said human is an infant.

9. The method according to claim 2 wherein said human is a child.

10. The method according to claim 2 wherein said human is elderly.

* * * * *

UNITED STATES PATENT AND TRADEMARK OFFICE
CERTIFICATE OF CORRECTION

| | |
|---|---|
| PATENT NO. | : 9,168,236 B2 |
| APPLICATION NO. | : 14/110214 |
| DATED | : October 27, 2015 |
| INVENTOR(S) | : Vincent Lotteau et al. |

It is certified that error appears in the above-identified patent and that said Letters Patent is hereby corrected as shown below:

In the Specification

Column 2, lines 42-51 should read as follows:

More particularly, the present invention relates to a method for inhibiting the replication capacity of an influenza virus in an infected cell comprising the steps consisting of contacting said infected cell with at least one compound selected from the group consisting of Gemcitabine, Obatoclax Mesylate, Docetaxel, HA-14, Alsterpaullone, GSK3B inhibitor VIII, GSK3B inhibitor XV, Indirubin 3'-monoxime, L glutathione reduced, Fluocinolone acetonide, Tirofiban, Topotecan hydrochloride, Clofarabine, Vinblastine, Menadione Crystalline and derivatives or analogues thereof.

Column 6, lines 42-46 should read as follows:

It is understood that the total amount per day can be administered in a single dose or can be administered in multiple dosing, such as twice a day (e.g., every 12 hours), three times a day (e.g., every 8 hours), or four times a day (e.g., every 6 hours).

In the Claims

Column 14, lines 43-51 should read as follows:

5. The method according to claim 1 wherein the influenza virus is selected from the group consisting of H1N1, H2N2, H3N2, and H5N1.
6. The method according to claim 2 wherein the influenza virus is selected from the group consisting of H1N1, H2N2, H3N2, and H5N1.
7. The method according to claim 3 wherein the influenza virus is selected from the group consisting of H1N1, H2N2, H3N2, and H5N1.

Signed and Sealed this
Twenty-third Day of February, 2016

Michelle K. Lee
*Director of the United States Patent and Trademark Office*